United States Patent
Papanastasiou et al.

(10) Patent No.: US 9,978,578 B2
(45) Date of Patent: May 22, 2018

(54) SEGMENTED LINEAR ION TRAP FOR ENHANCED ION ACTIVATION AND STORAGE

(71) Applicant: FASMATECH SCIENCE & TECHNOLOGY LTD., Oxford (GB)

(72) Inventors: Dimitris Papanastasiou, Athens (GR); Emmanuel Raptakis, Oxford (GB)

(73) Assignee: FASMATECH SCIENCE & TECHNOLOGY LTD., Oxford (GB)

(*) Notice: Subject to any disclaimer, the term of this patent is extended or adjusted under 35 U.S.C. 154(b) by 34 days.

(21) Appl. No.: 15/015,101

(22) Filed: Feb. 3, 2016

(65) Prior Publication Data

US 2017/0221694 A1    Aug. 3, 2017

(51) Int. Cl.
*H01J 49/42* (2006.01)
*H01J 49/00* (2006.01)

(52) U.S. Cl.
CPC ........ *H01J 49/4225* (2013.01); *H01J 49/426* (2013.01); *H01J 49/005* (2013.01); *H01J 49/0054* (2013.01)

(58) Field of Classification Search
CPC .... H01J 49/4225; H01J 49/426; H01J 49/005; H01J 49/0054
See application file for complete search history.

(56) References Cited

U.S. PATENT DOCUMENTS

| | | | |
|---|---|---|---|
| 6,483,109 B1 | 11/2002 | Reinhold et al. | |
| 6,753,523 B1 | 6/2004 | Whitehouse et al. | |
| 6,797,950 B2 | 9/2004 | Schwartz et al. | |
| 7,026,613 B2 * | 4/2006 | Syka | H01J 49/0095 250/282 |
| 7,034,292 B1 | 4/2006 | Whitehouse et al. | |
| 7,312,442 B2 | 12/2007 | Hansen | |
| 7,456,389 B2 * | 11/2008 | Kovtoun | H01J 49/4225 250/281 |
| 7,534,622 B2 | 5/2009 | Hunt et al. | |

(Continued)

OTHER PUBLICATIONS

Donald J. Douglas et al., "Linear Ion Traps in Mass Spectrometry", Mass Spectrometry Reviews, Rev. 24, pp. 1-29, 2005, US.

(Continued)

*Primary Examiner* — Eliza Osenbaugh-Stewart
(74) *Attorney, Agent, or Firm* — Franco S. DeLiguori; DP IP Group

(57) ABSTRACT

A linear ion trap includes at least two discrete trapping regions for processing ions, a RF electrical potential generator, a multi-output DC electrical potential generator, and a control unit. The RF electrical potential generator produces two RF waveforms each applied to a pair of pole electrodes of the linear ion trap forming a RF trapping field component to trap ions radially. The multi-output DC electrical potential generator produces multiple DC field components superimposed to the RF field component and distributed across the length of the linear ion trap to control ions axially. The control unit switches the DC electrical potentials and corresponding DC field components collectively forming a first trapping region populated with ions to alter ion potential energy from a first level to a second level, and enables a first ion processing step in at least one of the first and second levels.

21 Claims, 8 Drawing Sheets

(56) References Cited

U.S. PATENT DOCUMENTS

| | | |
|---|---|---|
| 7,737,396 B2 | 6/2010 | Chernushevich et al. |
| 7,755,034 B2 | 7/2010 | Ding |
| 7,847,248 B2 | 12/2010 | Collings |
| 8,680,463 B2 | 3/2014 | Loboda |
| 8,916,819 B2 | 12/2014 | Makarov et al. |
| 2006/0208187 A1 | 9/2006 | Murdehai et al. |
| 2008/0210860 A1 | 9/2008 | Kovtoun et al. |
| 2015/0160232 A1* | 6/2015 | Chen ................. G01N 33/6851 250/282 |

OTHER PUBLICATIONS

Tonya Pekar Second et al., "Dual-Pressure Linear Ion Trap Mass Spectrometer Improving the Analysis of Complex Protein Mixtures", American Chemical Society, vol. 81, No. 18, pp. 7757-7765, Sep. 2009, US.

Jae C. Schwartz et al., "A Two-Dimensional Quadrupole Ion Trap Mass Spectrometer", American Society for Mass Spectrometry, vol. 13, Issue 6, pp. 659-669, Jun. 2002, US.

Yuichiro Hashimoto et al., "Mass Selective Ejection by Axial Resonant Excitation from a Linear Ion Trap", American Society for Mass Spectrometry, vol. 17, p. 685, Jan. 2006, US.

F.A. Londry et al., "Mass Selective Axial Ion Ejection from a Linear Quadrupole Ion Trap", American Society for Mass Spectrometry, vol. 14, p. 1130, Jun. 2003, US.

\* cited by examiner

SEGMENTED LINEAR ION TRAP FOR ENHANCED ION ACTIVATION AND STORAGE

BACKGROUND

Field of the Invention

The technical field of the invention relates to ion analysis using mass spectrometry. More particularly, to the development of a segmented linear ion trap to enable an extended range of ion processing techniques applied sequentially and facilitated by controlling the RF and DC electrical potential of trapping regions. Specifically, to the development of electronics and associated new techniques for ion trap operation.

Background Information

Linear ion traps have evolved into extremely powerful and versatile analytical devices and constitute a significant and indispensible instrumentation section in modern mass spectrometry. Deployed as stand-alone mass analyzers or integrated in hybrid mass spectrometers, the range of tools and methods available for manipulating gas phase ions are remarkably wide. Linear ion traps are ideal platforms for developing and testing novel designs to achieve enhanced performance capabilities and further extend versatility. Reviews on linear ion trap instrumentation are concerned with 2-dimensional RF trapping fields and the properties of radial ion confinement, axial control of ion motion including approaches for coupling to mass analyzers [Douglas et al, Mass Spectrom Rev 24, 1, 2005].

The two main advantages of linear ion traps compared to the standard 3D quadrupole ion trap include reduced space charge effects due to the increased ion storage volume and enhanced sensitivity for externally injected ions due to higher trapping efficiencies [Schwartz et al, J Am Soc Mass Spectrom 13, 659, 2002]. Enhanced performance has been demonstrated in a dual-pressure linear ion trap where ion selection and fragmentation process are optimized independently [Second et al, Anal Chem 81, 7757 2009]. More complex arrangements involve mass selective axial ejection techniques either based on fringe fields to convert radial ion excitation to axial motion [Londry & Hager, J Am Soc Mass Spectrom 14, 1130, 2003] or on the use of vane lenses inserted between RF pole-electrodes and supplied with axial AC excitation waveforms [Hashimoto et al, J Am Soc Mass Spectrom 17, 685, 2006]. The activation-dissociation methods available are limited to Collision Induced Dissociation (CID) and Electron Transfer Dissociation (ETD) and so far no more than two activation methods can be performed in tandem in the same linear ion trap. Therefore, the development of novel designs capable of supporting a wide range of efficient activation-dissociation tools and methods and the ability to perform these sequentially is essential, particularly for the analysis of highly complex biological samples and proteins.

A concept design of a collision cell with multiple potential regions for storing and processing ions is disclosed in U.S. Pat. No. 7,312,442B2. Although the proposed ability to sequentially activate and dissociate ions using different techniques is highly desirable, the method neither involves injection of charged particle beams for dissociative interactions nor is concerned with adjusting the DC electrical potential and consequently the potential energy of the ions between multiple levels, which greatly facilitates control of the interaction energy to optimize activation-dissociation processes. Furthermore, advanced control of the DC electrical potential and also the ion potential energy are critical for efficient ion transfer between trapping regions including receiving and releasing ions with precise kinetic energy to and from a linear ion trap respectively. These new aspects require novel DC switching technology and methods disclosed in the present invention.

Techniques to control the interaction energy between ions stored in ion traps and externally injected electrons are disclosed in U.S. Pat. No. 7,755,034B2. In order to control the energy of the interaction in a linear ion trap three-state digital waveforms are employed where electrons are injected during the intermediate voltage state. In addition to the constrains in the mass range of the ions stored successfully in the ion trap imposed by three-state RF trapping, the voltage amplitude accessible for the intermediate state is also severely limited and so is the accessible energy range available during interaction. Another disadvantage of the method disclosed for operating a linear ion trap is the narrow time window for interactions to occur, which is limited to less than ⅓ of the waveform period. The method disclosed in the present invention alleviates all these problems by decoupling the properties of the RF trapping waveform from the electron source potential by the superposition of DC field components to control the potential energy of the ions independently and to any desired level. The mass range remains unaffected over an unlimited energy range and the time of interaction is maximized.

Overall, the need remains for an improved linear ion trap and methods for activating and dissociating ions sequentially in a single apparatus using different techniques and performed with high efficiency.

SUMMARY

A linear ion trap arrangement configured with multiple segments is disclosed providing at least two trapping regions formed by the superposition of multiple DC electrical field components to the main RF electrical field component. Preferably, a trapping region consists of at least three segments comprising four pole-electrodes and forming a quadrupole configuration. A trapping region may also consist of segments and end-cap electrodes. Opposite phase RF waveforms are applied to pairs of pole-electrodes to create the RF electrical field component distributed across the entire trapping volume to confine ions radially. Multiple DC electrical field components are formed by applying switchable DC electrical potentials to pole-electrodes or independent RF-free electrodes inserted between pole-electrodes to create trapping regions to facilitate axial control and also to define the potential energy of ions stored therein. Trapping regions are formed by lowering the DC electrical potential of one of the DC field components in a trapping region with respect to neighboring DC electrical field components creating a potential well. The terms RF electrical field and RF field are used interchangeably. The terms DC electrical field and DC field are also used interchangeably.

The linear ion trap of the present invention further requires alterations or switching of DC electrical potentials applied to generate the DC field components forming a trapping region between a first DC potential level and at least a second DC potential level. Switching of DC electrical potentials can also be performed between three or more DC potential levels. Preferably, the alterations or switching of the different DC electrical potentials of a trapping region is performed simultaneously.

Switching of DC electrical potentials and corresponding DC field components forming trapping regions can be exercised in the absence of ions. Switching of a DC field component between two levels is also exercised to release from or receive ions in a trapping region. Preferably, switching of a DC field component is exercised following alterations of the DC components forming a trapping region.

A direct consequence of controlling the DC electrical potentials and corresponding DC field components forming a trapping region is the concurrent alteration or switching of the potential energy of the ions stored therein. Therefore, the linear ion trap of the present invention further requires an alteration of the ion potential energy between a first potential energy level and at least a second potential energy level by raising or lowering, lifting or dropping the magnitude of the DC electrical potentials applied to generate DC field components forming a trapping region and further processing ions in at least one of the energy levels respectively.

Processing in a trapping region of the linear ion trap of the present invention includes activation of ions using externally injected reagent ions or reagent ions co-trapped with precursor ions, interactions with electrons, manipulation of the mass-to-charge ratio of ions preferably by electron detachment, proton attachment or charge reduction processes, interactions between ions and neutral molecules in ground or excited state, interactions with photons, excitation of ion motion using auxiliary AC waveforms or duty cycle variations of the RF trapping waveform, ion isolation using AC waveforms or duty cycle control, collisional activation dissociation, ion accumulation and transfer. Processing may involve one or more of the above functions to be performed simultaneously or sequentially.

It is desirable to control the energy of interaction between ions populating at least one trapping region of the linear ion trap and externally injected charged particles, for example ions and/or electrons. It is also desirable to inject charged particles in-through the trapping region to activate ions stored at a first potential energy level and subsequently alter or adjust the potential energy of processed ions to a second potential energy level to perform a second processing step. The second potential energy level may also facilitate transfer of ions from the first trapping region to a second trapping region or ejection toward a mass analyzer. The second processing step may also involve external injection of electrons and/or reagent ions for activation and dissociation experiments. The processing step performed in the first potential energy level may differ from the processing step performed in the second potential energy level of the first trapping region. Sequential processing steps in a trapping region can be performed by injecting electrons, while different activation-dissociation mechanisms can be enabled by adjusting the potential energy of the ions during sequential interactions at different energy levels. The potential energy of the ions can be adjusted to optimize processing in each of the first and second levels respectively. Processing steps in multiple potential energy levels can be executed during a processing cycle.

In one example, Electron Capture Dissociation (ECD) requires the potential energy of the ions to be less than 10 eV relative to the potential energy of the electron source whereas electron detachment to reduce mass-to-charge ratio forming multiply charged radical ions requires a potential energy in excess of 10 eV, preferably in excess of 30 eV. Electron Induced Dissociation (EID) via electronic-to-vibrational excitation requires electrons with even higher kinetic energies to be injected in the trapping region populated with ions and extending the interaction period. Controlling the potential energy of the ions between multiple energy levels allows for all these different activation-dissociation methods to be performed sequentially. New dissociation pathways become accessible by combing these techniques in a manner disclosed in the present invention.

The linear ion trap of the present invention further requires the application of a RF trapping waveform producing a substantially constant field during at least a portion of the waveform period to permit injection of charged particles with precise kinetic energy into the trapping region. Charged particles are electrons produced in an electron source or reagent ions produced in an ionization source. Charged particles can be injected periodically or continuously. Periodic injection of charged particles in the ion trap is controlled by a deflector synchronized with the trapping waveform.

In a preferred exemplary embodiment of the present invention, the linear ion trap comprises at least two trapping regions for processing ions. A first processing step involves trapping in a first potential energy level where ions are preferably but not exclusively activated or dissociated, subsequently lifting the potential energy of the ions in the first trapping region from a first level to a second level. Switching the DC level of one of the DC field components forming the first trapping region is applied to transfer ions to the second trapping region for additional processing at a new potential energy level or eject ions toward a mass analyzer or an ion mobility spectrometer. The second potential energy level of the first trapping region is preferably adjusted relative to the potential energy level of the second trapping region to suppress collisional activation during transfer. It is also desirable to process ions in the first and second trapping regions respectively at different potential energy levels and apply different processing steps. Lifting and dropping the potential energy of the ions in each of the trapping regions is necessary to transfer ions back and forth between the two trapping regions. For example, a second processing step can be performed at the second potential energy level of the first trapping region. Adjusting the potential energy of the ions stored in the first trapping region to a third level and switching one of the DC field components can be exercised to eject ions toward the second trapping region. Consecutive processing steps can be performed in the second trapping region at different potential energy levels. Products can be transferred back to the first trapping region or ejected toward a mass analyzer by controlling the level of DC electrical potentials forming the second trapping region in a synchronous manner and switching one of the DC field components for subsequent release of ions. At least one of the DC field components is switched between at least three different DC levels during a processing cycle.

The ability to alter or adjust the DC electrical potentials and corresponding DC field components between different levels in order to control the potential energy of the ions greatly facilitates multiple processing steps performed in different trapping regions of the linear ion trap at energy levels tailored to optimize specific processes. Potential energy alterations are essential for the optimization of activation-dissociation experiments by controlling the energy of interactions with externally injected charged particles and for transferring ions in neighboring trapping regions for further processing at different DC electrical potential levels. The enhanced functionality of the linear ion trap of the present invention is afforded by fast transitions of selected DC electrical potentials to control ion potential energy. Furthermore, adjusting the potential energy level of the ions is a highly efficient method to decouple the ionization source potential from the operation of the linear ion trap. Ejection of ions towards a mass analyzer or an ion mobility spectrometer can also be optimized independently.

The diversity of experiments enabled through advanced control of multiple DC electrical potentials to alter or adjust the potential energy of the ions in different trapping regions of the linear ion trap is practically unrestricted. For example, ions can be processed in a first trapping region at a first potential energy level. Lifting the potential energy and switching one of the DC field components of the first trapping region can be applied in a manner to accelerate ions to kinetic energies sufficient for collisional activation dissociation to occur inside the linear ion trap. Ions can be transferred and stored in a second trapping region whilst the DC field component of the first trapping region is relaxed to the original level. Switching of one of the DC field components in the second trapping region is preferably applied to receive and store ions efficiently therein. Re-acceleration is accomplished by lifting the potential energy in the second trapping region and switching the same DC field component to release ions back toward the first region extending the activation period in order to enhance the efficiency of dissociation. Oscillation of ions between trapping regions can be exercised independently or in combination with additional processing steps performed sequentially. It is desirable to decelerate energetic ions inside a uniform RF field and not by applying a stopping potential to end-cap electrodes, which are unsuitable for reflecting ions due to the presence of fringe fields associated with significant losses of higher mass ions. In this lift-switch mode of operation of the present invention the energy imparted to the ions upon collisions with background gas molecules can be varied considerably enhancing the efficiency of dissociation, particularly for high mass ions which are difficult to analyze with conventional slow heating CID methods.

In yet another preferred exemplary embodiment of the present invention, the linear ion trap comprises at least three trapping regions for processing ions. Most preferably each of the trapping regions is designed to support unique and independent processing functionalities. The ability to lift, reduce and adjust the potential energy of the ions through control of the DC electrical potentials and corresponding DC field components distributed across the linear ion trap is essential to optimize tandem activation-dissociation experiments and any other processing steps performed sequentially or simultaneously. Switching DC electrical potentials between at least three potential levels is also required to facilitate receiving and ejecting or transferring of ions between trapping regions.

The diversity of experiments accessible with at least three trapping regions establishes the linear ion trap of the present invention a powerful analytical tool. For example, AC auxiliary waveforms to isolate or excite to activate ions can be performed in a first trapping region, activation using externally injected charged particles can be exercised in a second trapping region, whereas additional activation steps or storage and accumulation of products species to enhance signal-to-noise ratio can be performed in a third trapping region. Differences in pressure demand imposed by all these different functions can be satisfied by fast gas pulses using pulse valve technology.

It is desirable to pulse gas to access elevated pressures over a short period of time while minimizing the gas load to neighboring vacuum compartments. Elevated gas pressures are necessary to enhance collision induced dissociation, cool ions via collisions during processing or transfer between trapping regions. Pulse gas also allows for operating the linear ion trap during ion isolation at low pressure. Preferably, the duration of a gas pulse for optimizing injection and transfer is less than 20 ms and at any instant in time pressure is uniform throughout the linear ion trap. The duration of a gas pulse for optimizing CID can be arranged to extend over a longer period of time. More than one pulse valve can be connected to the linear ion trap for delivering different gases. Most preferably, the linear ion trap is differentially pumped.

The DC electrical potential control and consequently the potential energy adjustment functionality of the present invention require switching at least one of the DC field components between three different DC levels. Switching DC electrical potential or DC voltages applied to segments between three or more DC levels is necessary to fully exploit the advantages associated with ion potential energy control in a linear ion trap designed with at least two trapping regions, most preferably in a linear ion trap designed with at least three trapping regions. Switching between three or more levels facilitates the releasing or receiving ions from or in a trapping respectively. Therefore, the linear ion trap of the present invention further requires the use of multiple state high voltage switching technology. In a preferred circuitry design high voltage MOSFET transistors are connected in series to enable DC switching between at least three levels of the DC electrical potential. In another preferred circuitry design a series of analogue multiplexers are employed where each multiplexer provides multiple output levels of each of the DC electrical potentials applied to generate the DC field components distributed across the linear ion trap. Individual analogue multiplexers or transistors connected in series can either be connected to individual segments to create DC field components for axial control of ion motion. Alternatively, RF-free electrodes immersed in the RF field can be biased to create the trapping regions for axial confinement and to transfer ions across the linear ion trap.

It is the purpose of the present invention to provide a linear ion trap capable of supporting at least two different activation-dissociation techniques, preferably at least three different activation-dissociation techniques performed sequentially and enabled through multiple transitions of the DC electrical potentials and corresponding DC field components to allow high level control of ion potential energy. These transitions are supported by advances in electronics circuitry design.

More specifically, there is provided a linear ion trap comprising at least two discrete trapping regions for processing ions, a RF generator for producing at least two RF waveforms, each RF waveform is applied to a pair of pole electrodes of said linear ion trap forming a RF trapping field component to trap ions radially, a multi-output DC voltage generator for producing DC electrical potentials to generate DC field components superimposed to the RF field component and distributed across the length of the linear ion trap to control ions axially and a control unit for switching each of the DC electrical potentials forming a first trapping region of said at least two trapping regions from a first level to a second level respectively. Switching DC electrical potentials of a trapping region between a first and a second level is exercised to alter or adjust the potential energy of the ions stored therein between a first and a second level respectively. Processing ions in at least one of the potential energy levels in a first trapping region is performed.

The multi-output DC voltage generator generates multiple DC electrical potentials applied to the linear ion trap and at least three DC electrical potentials are applied to create DC field components collectively forming a single trapping region where at least one of the DC electrical potentials is switched between three different DC levels. Switching is exercised to transfer ions from a first to a second trapping region to perform a second processing step. Switching is also exercised to alter the potential energy level of the ions stored in a second trapping region from a first to a second potential energy level. Processing ions in at least one of the potential energy levels in a second trapping region is performed. Switching one of the DC electrical potentials in a second trapping region between three different DC levels is exercised.

Ions can be released from a first toward a second trapping region with sufficient kinetic energy to perform collision induced dissociation. Trapping in the second trapping region is preferably exercised prior to releasing ions back to the first trapping region to extend the period of time where ions undergo energetic collisions with background gas molecules.

The linear ion trap further comprises a RF generator to generate waveforms comprising of substantially rectangular or trapezoidal voltage pulse trains to create RF trapping field components which remain substantially constant during a significant portion of the waveform period. The linear ion trap also comprises a source of charged particles and optics to form a beam of charged particles injected through a first trapping region containing ions at a first potential energy level, at a second potential energy level or at multiple potential energy levels.

The linear ion trap is configured to receive and thermalize ions from an ionization source at a first potential energy level, to processes ions at a second and a third potential energy level, and finally to eject ions thermalized at a fourth potential energy level toward a mass analyzer or an ejector coupled to a mass analyzer for measuring mass-to-charge ratios. Direct ejection from a trapping region of the linear ion trap to a mass analyzer is also envisaged.

A linear ion trap is provided comprising at least two discrete trapping regions for processing ions, a RF electrical potential generator for producing two RF waveforms, each applied to a pair of pole electrodes of the linear ion trap forming a RF trapping field component to trap ions radially, a multi-output DC electrical potential generator for producing multiple DC field components superimposed to the RF field component and distributed across the length of the linear ion trap to control ions axially, and a control unit configured to switch the DC electrical potentials and corresponding DC field components collectively forming a first trapping region populated with ions to alter ion potential energy from a first level to a second level, and to perform a first ion processing step in at least one of the levels.

The control unit is configured to switch at least one DC field component of DC field components collectively forming a first trapping region between three different DC electrical potential levels. The control unit is configured to switch at least one DC field component to transfer ions from a first trapping region to a second trapping region to perform a second processing step. The control unit is configured to switch the DC field components collectively forming a second trapping region to alter the potential energy of ions stored therein from a first level to a second level. The control unit is configured to switch at least one DC field component of DC field components collectively forming a second trapping region between three different DC electrical potential levels.

The RF waveforms comprise substantially rectangular voltage pulse trains. A pair of pole electrodes is configured to receive a beam of charged particles injected through a first trapping region populated with ions at a first potential energy level.

The control unit is configured to switch multiple DC field components to release ions from a first trapping region toward a second trapping region with sufficient kinetic energy to perform collision induced dissociation. The control unit is configured to switch at least one DC field component to eject processed ions toward a mass analyzer for measuring mass-to-charge ratio.

Methods for processing ions in a linear ion trap are also disclosed. In one exemplary embodiment, the method comprises providing a linear ion trap defining a trapping field with a substantially uniform pressure at a given instant in time, trapping ions in the trapping field produced by the superposition of a RF trapping field component for radial confinement of the ions and multiple DC field components for axial control of the ions, distributing the DC field components along the axis of the linear ion trap to form at least two discrete trapping regions, subjecting ions in a first trapping region at a first potential energy level to a first processing step, and switching the DC field components collectively forming the first discrete trapping region in a timely manner to alter the potential energy of the ions from a first level to a second level.

The method further comprises switching at least one DC field component of a first trapping region between three different levels to facilitate ion transfer to a second trapping region. The method further comprises altering the potential energy of the ions in the second trapping region from a first potential energy level to a second potential energy level and processing ions in at least one of the levels. The method further comprises subjecting ions to a second processing step in the second potential energy level of the first discrete trapping region. The method further comprises subjecting ions to third processing step in a first or a second potential energy level of the second discrete trapping region. The method further comprises producing the RF trapping field component by two opposite phase RF waveforms comprising substantially rectangular voltage pulse trains. The method further comprises injecting a beam of charged particles through the trapping region to activate ions in at least one of the first, second and third processing steps.

In another exemplary embodiment, a method for processing ions in a linear ion trap comprises providing a linear ion trap defining a trapping field at a substantially uniform pressure at a given instant in time, trapping ions in the trapping field produced by the superposition of a RF trapping field component for radial ion confinement and multiple DC field components for axial control of the ions, distributing the DC field components spatially to form at least two discrete trapping regions along the axis of the linear ion trap, subjecting ions in a first trapping region at a first potential energy level to a first processing step, subjecting ions in a second trapping region at a second potential energy level to a second processing step, transferring processed ions between trapping regions by switching DC field components collectively forming trapping regions to alter the potential energy of the ions stored therein, and switching at least one DC field component between three different DC electrical potential levels.

In yet another exemplary embodiment, a method for processing ions in a linear ion trap comprises providing a linear ion trap defining a trapping field with a substantially uniform pressure at a given instant in time, trapping ions in the trapping field produced by the superposition of a RF trapping field component for radial ion confinement and multiple DC field components for axial control of the ions, distributing the DC field components spatially to form at least three discrete trapping regions in said linear ion trap, subjecting ions in the first trapping region at a first potential energy level to a first processing step, subjecting ions in the second trapping region at a second potential energy level to a second processing step, subjecting ions in the third trapping region at a third potential energy level to a third processing step, transferring processed ions between trapping regions by switching DC field components collectively forming trapping regions to alter the potential energy of the ions stored therein, and switching at least one DC field component between three different DC electrical potential levels.

A method for processing ions in a linear ion trap according to another exemplary embodiment comprises a linear ion trap defining a trapping field produced by the superposition of a RF trapping field component for radial ion confinement and multiple DC field components for axial control of the ions, distributing the DC field components spatially to form at least two discrete trapping regions along the axis of the linear ion trap, subjecting ions in the first trapping region at a first potential energy level to a first processing step, altering the potential energy of the ions, and switching at least one DC field component between three different DC electrical potential levels to release ions from the first trapping region.

In another exemplary embodiment, the present invention also provides a method of moving ions along the axis of a linear ion trap. The method comprises generating a RF electrical potential for confining ions radially relative to the axis within a trapping region of the ion trap, generating multiple DC electrical potentials defining a trapping region for axially confining ions within the trapping region whereby the RF and DC electrical potentials collectively trap ions within the trapping region, simultaneously changing the DC electrical potentials of the first trapping region between a first level and a second level, and changing DC electrical potentials at the second level at one side of the trapping region to a value not exceeding the minimum DC electrical potential of the trapping region thereby permitting the release of ions confined therein for movement along the axis.

In the foregoing exemplary embodiment, the ion trap may comprises a plurality of segments arranged sequentially in an array extending parallel to the axis for generating and shaping the spatial profile of the DC electrical field. The method further includes providing a finite number of different substantially constant DC voltages for generating each DC electrical field and applying a respective one of the DC electrical voltages to a respective one of a plurality of segments of the ion trap.

DETAILED DESCRIPTION

Figure 1A:
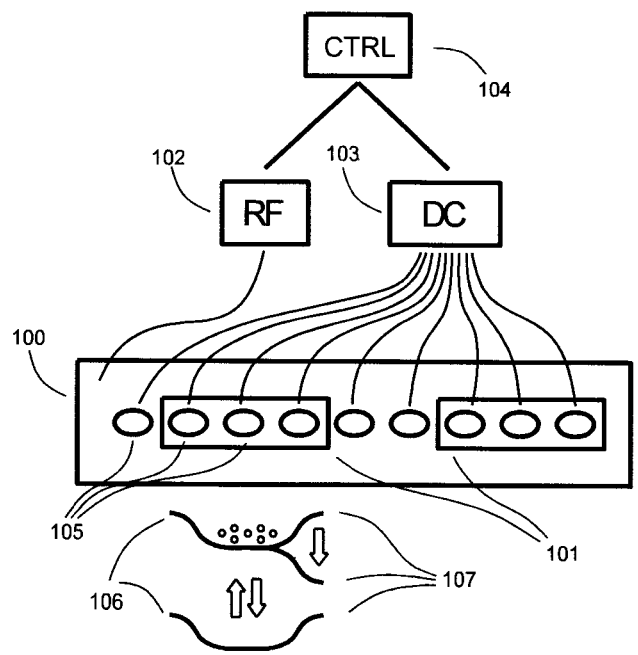
FIG. 1A is a schematic diagram of the linear ion trap system including the RF and DC generators and a control unit to control RF and DC electrical potentials and ion potential energy.

A general description of a linear quadrupole ion trap of the present invention is provided with reference to FIG. 1A. The linear ion trap 100 is connected to a RF generator 102 producing two RF waveforms, each applied to a pair of pole electrodes of the linear ion trap forming a RF trapping field component to trap ions radially. The linear ion trap 100 is also connected to a multi-output DC generator 103 producing multiple DC electrical potentials forming multiple DC field components 105 superimposed onto the RF field component and distributed across the length of the ion trap to control ions axially. A control unit 104 (e.g., FPGA control unit 346 further described below with reference to FIG. 3C) is used to define the characteristics of the RF waveforms and also the timing and the switching of the DC electrical potentials between different levels. The linear ion trap is preferably configured with two discrete trapping regions 101 for processing ions therein. The levels of the DC field components forming a discrete trapping region are arranged to form a potential well 106 to confine ions axially and the control unit is configured to collectively adjust or alter the level of the potential well in a timely manner. The control unit 104 is also configured to switch a DC field component between three different levels 107.

Figure 1B:
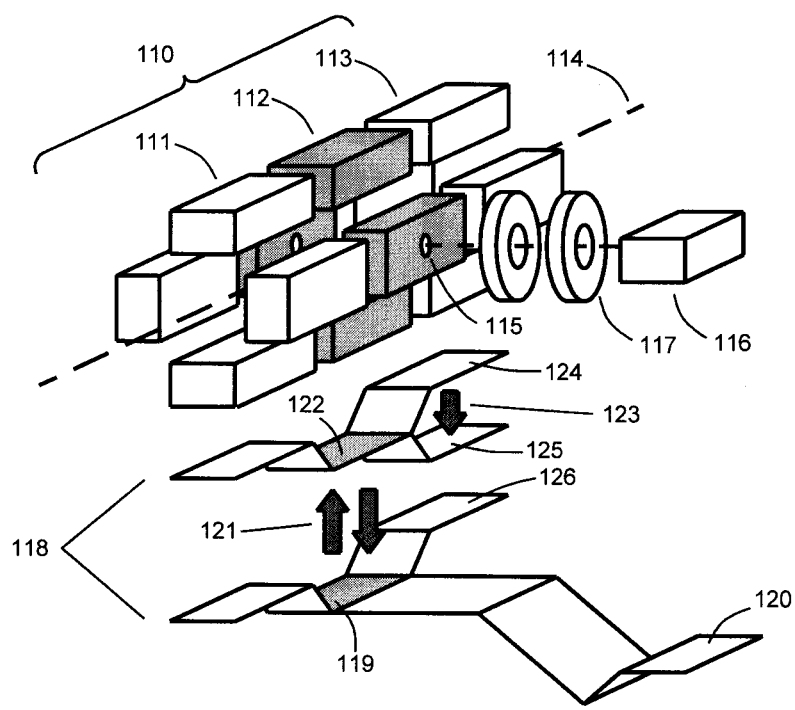
FIG. 1B is a perspective view of a segmented linear ion trap configured with a single trapping region and associated transitions of the DC electrical potential to control ion potential energy.

A description of a linear quadrupole ion trap is provided with reference to FIG. 1B. The linear quadrupole ion trap 110 comprises three segments 111, 112 and 113 where each segment is formed by two pairs of pole-electrodes and each pair is supplied with opposite phase RF waveforms to form the RF field component for trapping ions radially. All segments share a common axis 114 and collectively define a trapping region for processing ions. Independent DC electrical potentials are applied to segments forming three DC field components respectively for axial control of the ions. The magnitude of the DC field component applied to the central segment 112 is lower relative to the neighboring DC field components to form a potential well and confine ions axially. The central segment is also designed with inlet apertures 115 on the pole-electrodes to accept charged particles generated externally in a charged particle source 116. Injection of charged particles through the apertures 115 on the poles is facilitated by a focusing lens system 117.

The transitions of the DC electrical potential or the potential energy surface along the axis of the linear ion trap of the present invention are also shown at 118. Ions are processed and/or activated by injecting charged particles with the desired kinetic energy determined by the DC electrical potential level of the charged particle source 120 relative to the first DC electrical potential level 119. The potential energy of the ions is subsequently raised 121 to a second energy level 122 where a second activation processing step can be performed. In this basic configuration switching 123 of the DC field component applied to segment 113 between three different DC levels or DC electrical potentials 124, 125 and 126 is necessary to facilitate ion transfer or ejection. The first DC electrical potential 126 is adjusted to a level higher than the potential applied to the central segment 122 to confine ions axially, the second potential 124 is a result of alterations of the of the level of the potential well 121 to facilitate ion processing at a second DC potential level 122 while the third DC potential level 125 is applied to release ions from the central segment 112. Switching DC electrical potentials between three different levels is necessary to control the kinetic energy of the ions, for example matching the acceptance energy of a mass analyzer during ejection of ions stored in the potential well or controlling the energy in binary collisions with buffer gas molecules during transfer.

The DC electrical potential control functionality 121 greatly facilitates multiple processing steps to be realized by adjusting the potential energy of the ions to optimum levels for injection of charged particles with different kinetic energies. In each activation-dissociation step the energy of the interaction is determined by the relative DC potential level the ions stored at in the central segment 112 and the DC potential level of the charged particle source 116. For example, electron capture dissociation, electron induced dissociation and electron detachment for charge state manipulation can all be performed in the same trapping region by simple adjustments of the DC electrical potential ions are stored at in the trap between three different levels.

Figure 2:
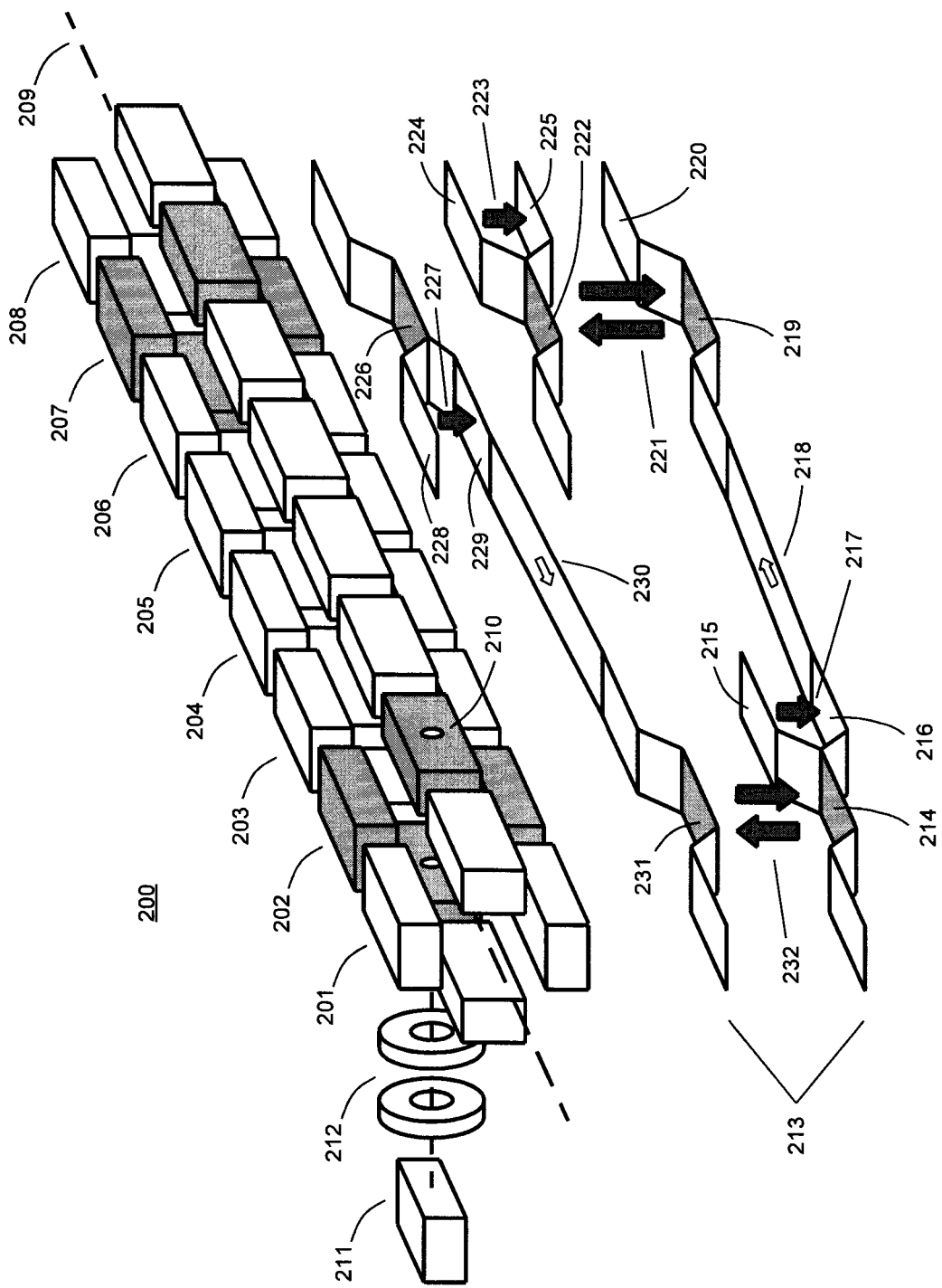
FIG. 2 is a perspective view of a segmented linear ion trap configured with two trapping regions and associated transitions of the DC electrical potential to control ion potential energy.

A description of a preferred exemplary embodiment of the present invention is provided with reference to FIG. 2. The linear quadrupole ion trap 200 consists of two trapping regions formed in segments 202 and 207, entrance-end and exit-end guard segments 201 and 208 respectively and intermediate guard segments 203-206 having a common axis 209 and collectively defining a trapping volume for processing ions. The trapping region formed in segment 202 is designed with inlet apertures 210 on a pair of pole-electrodes. A charged particle source 211 for injecting charged particles through a focusing lens 212 is connected externally to the linear ion trap 200. The second trapping region in segment 207 is preferably supplied with AC auxiliary waveforms to perform ion isolation and excitation of ion motion for collisional activation or dissociation.

The transitions of the potential energy surface of the segmented linear ion trap 200 are also shown 213. A processing cycle may include transferring ions into the linear ion trap in the first trapping region in segment 202 at a first DC electrical potential level 214. Ions introduced into the linear ion trap can be pre-selected using a quadrupole mass filter. Ion processing including activation and dissociation using externally injected charged particles generated in the particle source 211 is performed at a first potential level 214 or any other level necessary to optimize the efficiency of the process. Subsequently, the DC potential applied to the guard segment 203 is switched 217 between levels 215 and 216 to transfer ions to the second trapping region in segment 207 for subsequent processing at a different DC potential level 219.

A weak DC gradient 218 can be established between trapping regions to minimize energetic collisions with background gas molecules. Ion transfer can be performed at constant background pressure or during a gas pulse. Fast ion thermalization via collisions is achieved during a gas pulse or at constant elevated pressure. In contrast, ion thermalization at lower pressure is accomplished over an extended period in time where ions oscillate between trapping regions. Switching the DC potential 220 applied to the exit-end guard electrode 208 to a higher level is required to prevent ions from leaking out through the second trapping region of the ion trap 200.

Processing in the second trapping region in segment 207 may involve any of the processing steps performed using AC auxiliary waveforms, for example ion isolation or excitation of ion motion for collisional activation. The potential energy of ions selected using AC auxiliary waveforms or product ions generated in segments 207 or 202 can be raised 221 to a new level 222 for subsequent release toward a mass analyzer. The ejection process requires additional switching 223 of the DC electrical potential applied to segment 208 between levels 224 and 225. Alternatively, the potential energy of selected or product ions is raised to a higher level 226 for efficient transfer back to the first trapping region in segment 202. Transfer requires additional switching 227 of the DC potential applied to segment 206 between levels 228 and 229. Similarly, a weak DC gradient 230 is preferably established during transfer of ions between segments 207 and 202. Ions are trapped and further processed at the new DC electrical potential level 231. Processing can also be performed at a different level by switching 232 the DC field components in the first trapping region to a new level. Relaxing or raising the potential energy of the ions to the original level 214 in the first trapping region is necessary to optimize ion transfer to the second trapping region. The processing cycle described here can be repeated using the same or new processing steps.

The significant advantage of the ion potential energy control functionality enabled by DC switching of electrical field components between multiple levels during a single experimental cycle described with reference to FIG. 2 allows for elaborate multiple-stage or tandem in space and in time activation dissociation experiments to be performed efficiently. More importantly, the ion potential energy control functionality offers the unique advantage to select different activation dissociation tools and methods to be applied in each step of an experimental cycle without imposing restrictions in the energy of interaction between charged particles and ions or any other restrictions with regard to the energy acceptance requirements imposed by neighboring ion optical elements including ejection to a mass analyzer and an ion mobility spectrometer.

With reference to FIG. 2, multiple processing steps can be performed in the first trapping region simultaneously or sequentially, at the same or at different DC electrical potential levels using a single or different charged particle beams operated in a pulsed or in a continuous manner. Pulsed injection of charged particles in a trapping region requires gating to be applied. Gating is preferably synchronized with the phase of the trapping waveform. Two processing steps can be exercised in a single trapping region simultaneously, for example the application of AC auxiliary waveforms for excitation of ion motion and injection of electrons for ion activation and dissociation. Excitation of ion motion of selected ions during electron irradiation can be used to control the kinetics of activation or to minimize charge reduction and neutralization of ions. Additional charged particle sources can be coupled to different trapping regions of the linear ion trap. Processing in different trapping regions can be performed simultaneously or sequentially using the same or different group of ions.

In the example disclosed with reference to FIG. 2, the DC electrical potentials forming the DC field components are applied directly to the segments through resistors and capacitors. It is also desirable to DC bias independent electrodes inserted between RF pole-electrodes to superimpose the DC field components to the RF field component across the linear ion trap.

Figure 3A:
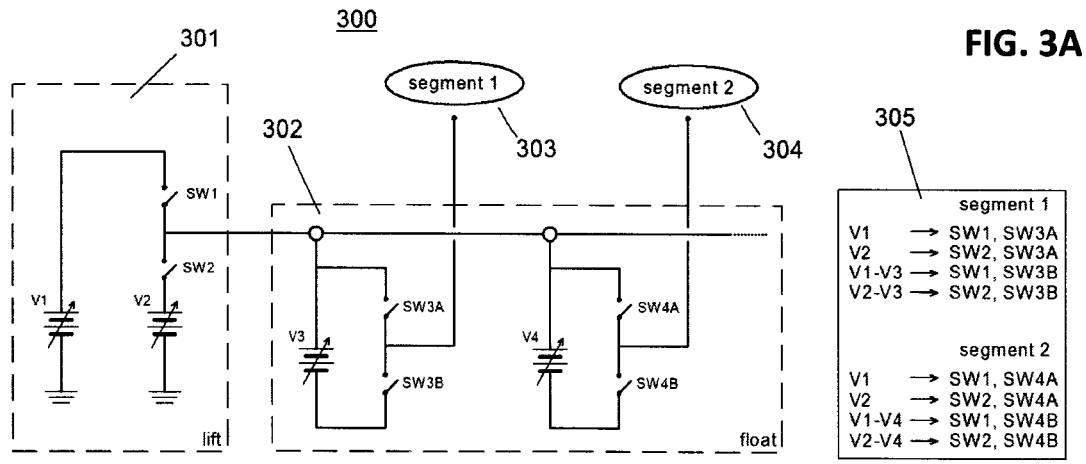
FIG. 3A is a circuitry diagram of switching electronics to control DC field components between multiple levels.
Figure 3B:
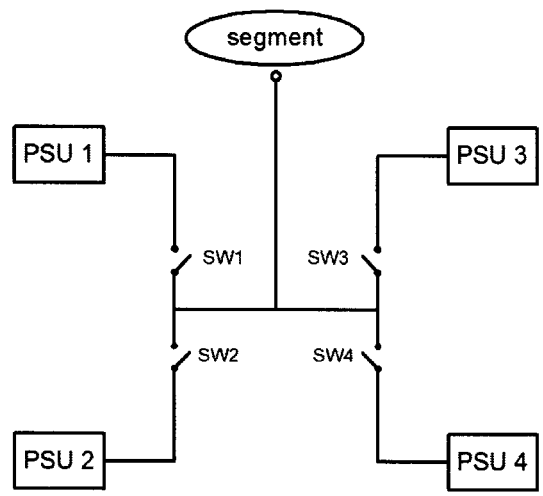
FIG. 3B is a circuitry diagram of switching electronics to control DC field components between multiple levels.
Figure 3C:
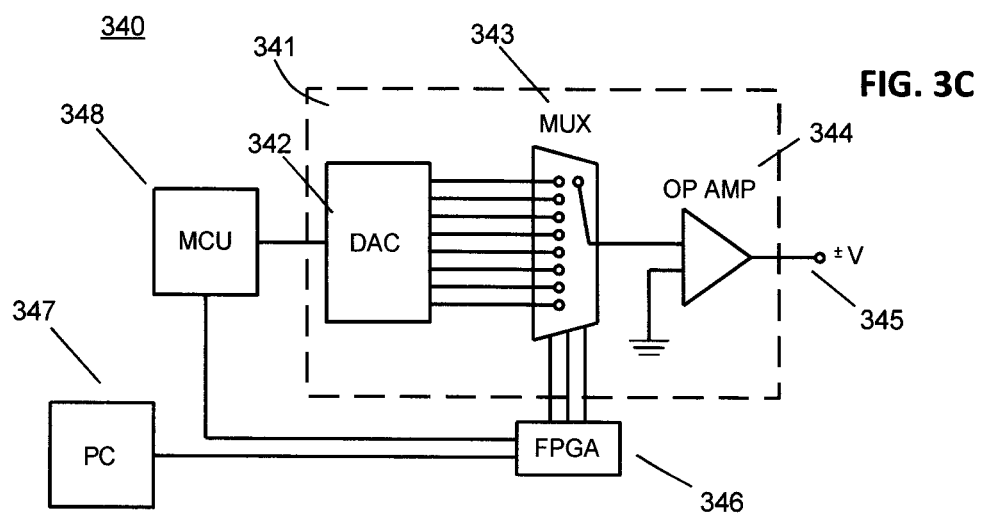
FIG. 3C is a circuitry diagram of switching electronics to control DC field components between multiple levels.

Circuitry diagrams of the present invention to enable multiple state switching of DC electrical potentials and facilitate the ion potential energy control functionality are presented in FIGS. 3A, 3B and 3C. FIG. 3A shows a circuitry diagram of the switching design 300 of the invention. In this example only two segments 303 and 304 of the linear ion trap are shown for simplicity and connected to a switching card 302, which is floated onto a second lift card 301. The lift card is designed to switch DC potentials or DC voltages applied to the segments between two different levels determined by the voltage output of two independent power supply units V1 and V2 respectively. The lift voltage is determined by switches SW1 and SW2 and the voltage output of the power supplies. The output of the lift card is connected to a third power supply unit V3 and an additional set of switches SW3A and SW3B in series and finally connected to the first segment 303. Similarly a fourth power supply unit V4 and switches SW4A and SW4B are also connected in series with the lift card and determine the voltage applied to the second segment 304. Table 305 summarizes the possible DC electrical potentials or DC voltage output levels that can be applied to each of the first and second segments respectively.

The float card 302 can accommodate additional pairs of switches and power supply units to connect to additional segments or independent DC electrodes of the linear ion trap. The float cards can be connected in series to the same or different lift cards. Grouping of specific float cards in series with two or more lift cards connected to individual segments maybe desirable to facilitate fast and independent switching of the DC field components in each of the trapping regions established across the linear ion trap. The polarity of the power supply units in both lift and float cards can be varied accordingly.

FIG. 3B shows another possible arrangement of four switches and the corresponding power supply units that can be employed for fast switching the voltage applied to a single segment between four different levels. This switching configuration can be floated on an independent lift card.

Processing cycles where more than three DC electrical potentials, DC voltages or levels of the DC field components are necessary to facilitate multiple-stage sequential activation dissociation, achieve efficient ion transfer between trapping regions, as well as receive ions and transfer products to the mass analyzer with the appropriate kinetic energy. More importantly, multiple DC state switching enables precise control of the potential energy of the ions through adjustments of the DC electrical potentials and corresponding DC field components across segments in a synchronous manner.

FIG. 3C shows a preferred electronics circuitry diagram 340 designed to apply eight different DC voltage levels to a single segment of the LQIT during the course of a processing cycle. The board 341 is populated with a DAC 342 driving an analogue multiplexer (MUX) 343 with eight output DC states connected to an operational amplifier 344, which in turn is connected through leads and vacuum feedthroughs 345 to a single segment. Both positive and negative potentials can be generated, typically limited to ±225V by the model of the operational amplifier. The number of DC states is typically controlled through a PC unit 347 which is connected to the FPGA (Field-Programmable Gate Array) control unit 346. The FPGA control unit 346 provides the control signals to the multiplexer and also forwards information to the microcontroller unit 348 for the DAC to generate the appropriate DC voltage levels. A second board identical to board 341 connected to the same MCU 348 and controlled in a synchronous manner through the FPGA control unit 346 is required for driving a second segment. Combinations of multiplexers and bidirectional switches are also advantageous for facilitating complex switching and advanced ion potential energy control. The FPGA control unit is further configured to control the characteristics of the substantially rectangular opposite phase RF waveforms including the RF amplitude, frequency and duty cycle. The FPGA control unit is also configured to control the properties of the auxiliary AC waveforms preferably applied in dipolar mode.

An exemplary embodiment of the present invention is described with reference to FIG. 4. The schematic diagram of the instrument 400 shows a segmented Linear Quadrupole Ion Trap (LQIT) attached to an atmospheric pressure interface where ions are transferred by intermediate pressure, gas dynamically optimized ion optics, through a RF ion guide into a subsequent vacuum region incorporating a preferred embodiment of the present invention. Ion mass-to-charge is measured using an oTOF mass analyzer.

Ions are generated by electrospray ionization 401 and sampled through a capillary inlet 402 into a first vacuum compartment 403 accommodating the aerolens 404. The function and properties of the aerolens are described in WO2014001827 and EP 2864998A2, the disclosures of which are incorporated herein by reference in their entirety. In brief, the supersonic jet 405 discharges into the bore of the aerolens, which is dimensioned to restrain radial expansion of the gas to form a laminar subsonic gas flow entraining charged clusters and ions. Pressure in the first vacuum compartment 403 is maintained at >1 mbar, preferably >10 mbar pressure using a mechanical pump 406 to enlarge the inlet system and enhance sampling efficiency from the ionization source. Ions are directed through a lens system 407 into a RF octapole 408 described in U.S. Pat. No. 9,123,517(B2), the disclosure of which is incorporated herein in its entirety. The RF octapole combines an octapolar field distribution 409 to capture ions at the entrance of the ion guide and a quadrupolar field distribution 410 to compress ions radially and maximize transmission through the differential aperture 411. A turbomolecular pump 412 is connected to a vacuum compartment 413 accommodating the RF octapole 408 to achieve a pressure in the range of $10^{-3}$-$10^{-2}$ mbar. Ions are kinetically thermalized in the RF octapole and transmitted through differential apertures 411 into the linear ion trap 414 of the present invention for processing. After processing ions are released from the LQIT through a RF hexapole ion guide 431 disposed in a subsequent vacuum compartment 433 evacuated by a turbomolecular pump 432 toward an orthogonal TOF mass analyzer 437 operated at high vacuum controlled by a turbomolecular pump 438. In this preferred configuration ions are transferred from the hexapole 431 through a set of differential apertures 433 into a high vacuum lens 434, a slicer 435 and finally undergo orthogonal acceleration by the application of high voltage extraction pulses to the electrodes of the orthogonal gate 436.

Figure 4:
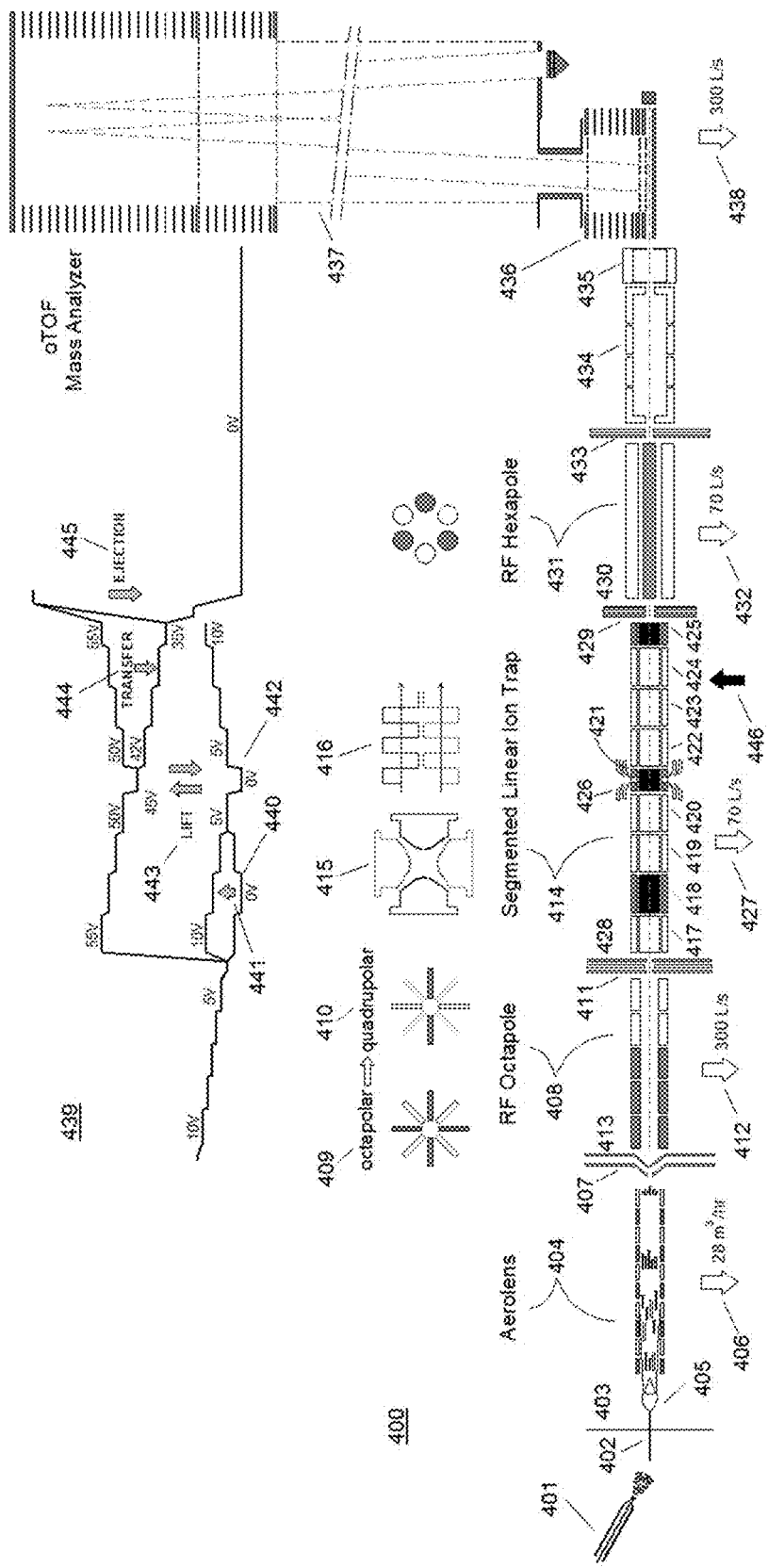
FIG. 4 is a schematic diagram of a mass spectrometer configured with a segmented linear ion trap including the transitions of the DC electrical potential profile to control ion potential energy.

In the embodiment shown in FIG. 4. the LQIT is constructed with hyperbolic pole-electrodes 415. Substantially rectangular trapping waveforms with 180° degree phase shift 416 are applied to opposite pole-electrodes. Rectangular or other types of trapping waveforms forming a substantially constant RF trapping field component during part of the waveform period are necessary for efficient interactions between trapped ions and externally generated ions and electrons. The LQIT is preferably encapsulated into a differentially pumped region 428 connected to a turbomolecular pump 427. Pulse valves 446 to dynamically control pressure in the trapping region and leak valves to control background pressure are connected to the LQIT. The LQIT is preferably disposed in vacuum compartment 430 accommodating the RF hexapole 431 and operated at lower pressure. Scattering of ions during ejection from the LQIT is therefore minimized and so is the axial kinetic energy spread.

The LQIT is designed with nine segments 417-425 where each segment is supplied with a switchable DC electrical potential to form trapping regions in segments 418, 421 and 425. Processing in the first trapping region in segment 418 involves ion collection and storage, ion accumulation, excitation of ion motion for isolation of a single mass-to-charge ratio or multiple precursor ions, slow heating collision induced dissociation using dipolar excitation, broadband excitation or DC dipolar excitation methods, activation without driving ions to dissociation and combinations thereof. The third trapping region in segment 425 is designed for storing and accumulating product ions prior to ejection toward the oTOF pulser 436 with the appropriate energy, satisfying the demand imposed by downstream optics and the mass analyzer. In a simple mode of operation raising the potential energy of the ions stored in segment 421 above the potential applied to segment 425 and subsequently switching appropriate DC field components is exercised to transfer ions efficiently between trapping regions.

Enhanced CID efficiency is obtained by superimposing auxiliary AC waveforms, preferably but not exclusively applied in dipolar mode, to the RF electrical field produced by substantially rectangular RF waveforms confining ions radially and by adjusting the duty cycle to values other than 0.5. Variations in the duty cycle are used to generate asymmetric and substantially rectangular waveforms to fine control the properties ion motion within the ion trap by creating an asymmetric ion motion. Most preferably, the direction of the asymmetric ion motion produced by varying the duty cycle of the RF waveforms is aligned relative to the direction of dipolar excitation to maximize the kinetic energy of ion vibrations in the ion trap without causing unwanted ejection. The energy deposited to the ions in the presence of a buffer gas under such trapping conditions is enhanced and so is fragmentation efficiency.

In another preferred configuration a first symmetric RF waveform is applied to the first pair of pole-electrodes and a second asymmetric waveform is applied to the second pair of pole-electrodes and further combined with an AC auxiliary waveform to excite ion motion to enhance the efficiency of CID. Applying a first symmetric RF waveform and a second opposite phase asymmetric RF waveform to the first and second pairs of pole-electrodes of a given segment of the ion trap respectively creates a second fundamental secular frequency of the ion motion and permits higher amplitude excitation waveforms to be applied without causing unwanted ejection. The duty cycle offset between the RF waveforms, excitation frequency and amplitude and also the q parameter of the ions on the stability diagram can be tuned to enhance the efficiency of CID.

Activation using electrons and reagent ions injected into the LQIT is performed in the second trapping region in segment 421. Examples of ion activation using externally generated charged particle beams include ECD, EID, electron detachment to reduce m/z ratio of precursor species producing multiply charged radical ions and other types of ion-electron interactions. External injection of reagent ions for ion-ion collisional activation and ion-ion reactions is also allowed. Ion-molecule reactions to form adduct species and fragments in addition to photo-fragmentation experiments can also be performed in segment 421.

In the case where interactions between trapped ions and electrons are considered, it is desirable to adjust first the DC field components forming the second trapping region to levels sufficiently lower compared to the potential energy level electrons are generated at to establish energetic interactions sufficient to detach electrons, create multiply charged radical species and reduce the m/z ratio of precursor ions. Efficient production of multiply charged radical ions is desirable to enhance activation dissociation experiments performed in subsequent processing steps. For example, subjecting multiply charged radical ions to CID and ECD experiments is expected to open up new dissociation pathways and enhance the analytical information currently available with existing activation-dissociation tools and methods. Controlling the potential energy of the ions during the course of an experiment is the most critical aspect enabling different activation tools to be employed sequentially.

It is also suitable to perform EID experiments by extending irradiation period of precursor ions with energetic electrons. Electronic-to-vibrational energy transfer is an alternative method to produce CID type ions and obtain enhanced sequence coverage. It is also possible to perform charge reduction experiments by irradiating multiply charged precursor ions with slow electrons. These functions and associated dissociation pathways become easily accessible by adjusting the potential energy level of the ions through alterations of the DC electrical potentials and corresponding DC field components superimposed onto the RF trapping field forming trapping regions for processing ions.

Producing multiply charged radical ions from precursor ions using energetic electrons or performing charge state reduction experiments are both efficient in controlling the charge state distribution of the ions. In this type of experiments frequency jumps of the RF trapping waveform are required to perform subsequent activation steps. For example electrons can be injected in the second trapping region at a first DC electrical potential level to generate multiply charged radical ions with reduced m/z ratios. The potential energy of product ions can then be lowered to levels sufficient for ECD to be performed. The m/z ratio of the multiply charged radical species produced in a first processing step and subsequently subjected to ECD can be matched to the m/z ratio of the ECD products to cover the widest range of m/z ratios stored successfully in the trap. This method enhances the analytical information that can be extracted during the course of a single experiment.

In another mode of operation of the present invention shown in FIG. 4, reagent ions generated in a discharge ionization source or by means of Electrospray Ionization (ESI) or other ESI variants known to those skilled in the art are introduced into the LQIT for ion-ion activation and ion-ion reaction experiments. Similarly, it is desirable to control the energy of the interaction between reagent and precursor ions, most preferably scan the energy of interaction by adjusting the potential energy of the ions in segment 421 to optimize product ion formation. Adjusting the DC field components in the second trapping region to identify optimum conditions for activation-dissociation studies is a more straight forward approach than adjusting the potentials applied along the entire reagent ion optical line.

The application of trapping waveforms, which exhibit a constant RF trapping field component over part of the waveform period greatly facilitates external injection of ions and electrons into the LQIT. Reagent ions and electrons can be injected in the trapping region with precise kinetic energy to optimize activation and dissociation experiments. It is the scope of the present invention to tune the energy of activation and dissociation by adjusting the potential energy of the ions stored in the second trapping region in segment 421 over a very wide range or between different levels. It is also the scope of the present invention to provide new tools and methods to perform ion activation experiments simultaneously and sequentially to enhance the analytical information extracted during the course of a multiple-stage activation-dissociation experiment. Most importantly, the different activation techniques, which involve interactions with externally injected charged beams, can be optimized independently and new dissociation pathways become available through alterations of the potential energy of the ions.

It is also desirable to perform different activation processes simultaneously for example irradiating ions with photons and electrons, or photons in the presence of reagent molecules. Reagent molecules are preferably introduced into the LQIT using a pulse valve and exhibit a residence time of the order of 10-100 ms.

In another preferred mode of operation, ions are stored using a two-state substantially rectangular trapping waveform and irradiated by reagent ions or electrons during a first half of the waveform period and with electrons during the second half to generate two different types of fragment ions simultaneously. The potential energy of the ions and products can be maintained constant or switched from a first level to a second level to adjust the energy of ion-ion and ion-electron interactions independently.

Interactions between ions stored in the LQIT in the second trapping region in segment 421 and externally generated charged particles and photons is facilitated by apertures on two opposite pole-electrodes in segment 421. Preferably, during the course of an experiment electron or reagent ion source optics are operated at fixed potentials and optimized for maximum transmission through the lens system 426 and through the exit aperture on the opposite pole-electrode to minimize surface contamination and charging. Focusing of ions and electrons through the apertures is accomplished in part by appropriate selection of voltages applied to the focusing lenses 426.

Different activation-dissociation procedures, especially those utilizing externally injected charged particle beams and in combination with standard fragmentation techniques become apparent only after realizing the possibility to switch and control the DC electrical potentials and as a result the potential energy of the ions between different levels in different trapping regions of the LQIT in order to fine tune interaction energies and also transfer ions efficiently. All the new methods are facilitated by advances in electronics as disclosed in the present invention in FIGS. 3A, 3B and 3C.

An example of a switching sequence of the DC profile 439 across the LQIT where at least one segment is switched between three different DC levels during the course of an experiment is presented in FIG. 4. Ions are transferred and accumulated in the first trapping region by lowering the DC electrical potential 440 in segment 418 relative to the DC potentials applied to neighboring segments. Ions are mass selected using AC auxiliary waveforms applied in dipolar mode to a single pair of pole-electrodes. After the completion of the first processing step precursor ions are transferred to the second trapping region in segment 421 by switching the DC field components 441 across the first three segments of the LQIT, 417, 418 and 419. Ions stored in the potential well 442 are subjected to a second processing step using external injection of energetic electrons to form multiply charged radical ions. This is accomplished by lifting the potential energy of ions 443 while the electron source is maintained at ground potential. A third processing step is performed by dropping the potential energy 443 of product ions to levels appropriate for ECD. In this example electron detachment to form multiply charged radical ions is performed with ~45 eV electrons and ECD with ~1 eV electrons. Finally, lifting the ions to the same energy level and switching DC potentials applied to segments 422-425 is applied to transfer ions 444 to the end segment 425 to optimize ejection 445 toward the oTOF mass analyzer.

Different experiments based on the same switching sequence can be performed, for example ions can be received in the potential well 440 and subjected to ECD without prior irradiation with energetic electrons. A deflector is synchronized with the transitions of the DC profile to prevent electrons from entering the trap when the potential energy of the ions stored in segment 421 is not appropriate for ECD to take place. Subsequently, ECD products ions can be transferred to segment 418 for isolation-selection of new precursor species and slow heating CID enabled by advanced control of DC electrical potentials and the switching methodology disclosed in the present invention.

Control of the DC electrical potential in populated trapping regions decouples the energy imparted to the ions during interactions with externally generated electrons and the requirements imposed for ion transfer and ejection from the trap. Potentials applied to segments can be freely adjusted to any level or multiple levels during a single experiment and this is made possible by advancements in electronics and the circuitry disclosed in the present invention.

Figure 5:
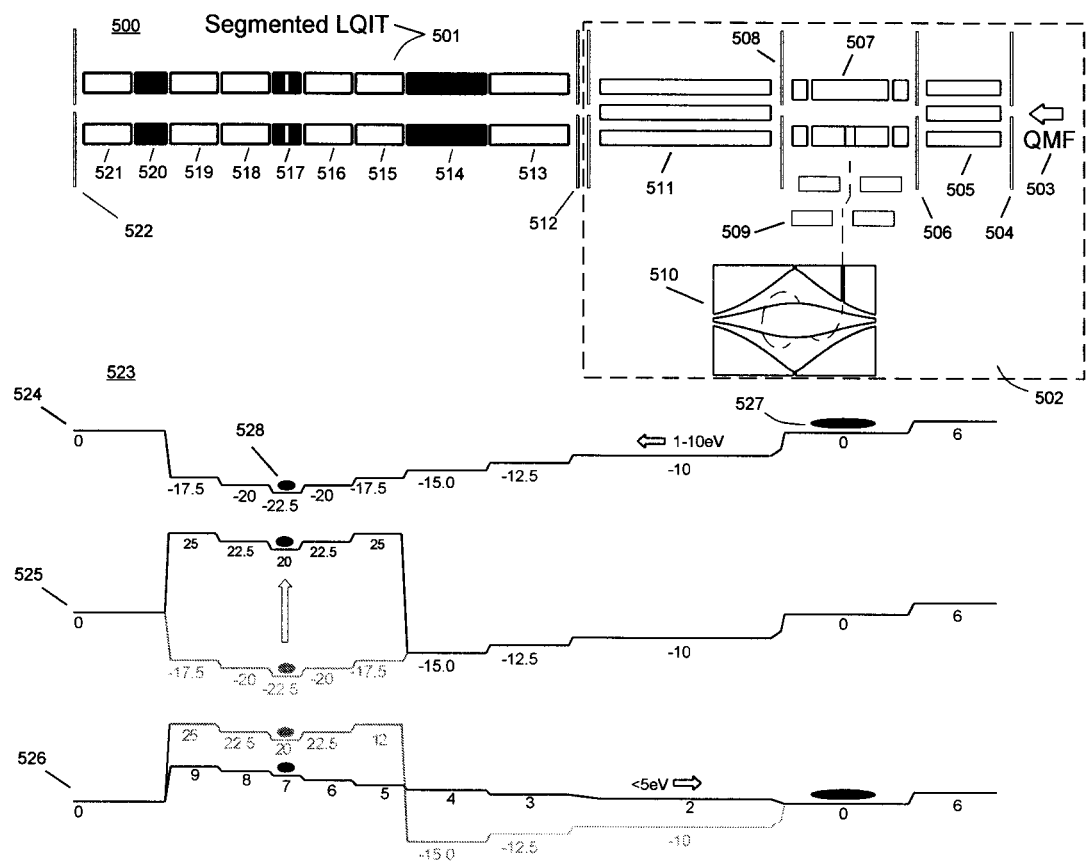
FIG. 5 is a schematic diagram of a mass spectrometer configured with a segmented linear ion trap including the transitions of the DC electrical potential profile to control ion potential energy.

Another exemplary embodiment of the present invention is shown in FIG. 5. The schematic diagram of the instrument 500 shows the segmented LQIT 501 attached to a mass spectrometric platform 502 which incorporates an orbitrap mass analyzer 510. Typically ions are mass selected in a Quadrupole Mass Filter (QMF) 503 and pass through differential apertures 504, 506 and a hexapole ion guide 505 to an ejection trap 507. Ions are subsequently injected through a deflector lens 509 into the orbitrap 510 for mass analysis or transferred axially to a RF hexapole 511 for collisional activation-dissociation. Ions can be transferred to the segmented LQIT 501 for a more comprehensive activation-dissociation analysis by lowering potentials applied to the differential aperture lenses 512. The LQIT is preferably differentially pumped and gas can escape only through apertures on pole electrodes and two end-electrodes disposed on either end of the LQIT, 512 and 522. The LQIT can be entirely immersed into a separate external vacuum compartment evacuated by a second turbo pump. Pulse valves, leak valve and a pressure gauge are preferably connected to the LQIT to control and monitor pressure.

The segmented LQIT in this exemplary embodiment is designed with nine segments in total 513-521 and three trapping regions formed in segments, 514, 517 and 520. The length of each of the active segments is optimized to perform specific functions with high efficiency. The first trapping region centered on segment 514 is extended in length to accommodate a larger number of charges and minimize space charge effects and related frequency shifts in order to perform resonance excitation for isolation of single or multiple precursor ions with high efficiency. Segment 514 is also designed to perform slow heating CID of single or multiple precursor ions during pulse gas introduction or under static background pressure. CID excitation can be performed with waveforms designed with single or multiple excitation frequencies. Other typical experiments with FNF or SWIFT waveforms applied to segment 514 may include multiple precursor selection, multiple precursor excitation and ion ejection using waveforms designed with single or multiple notches across the secular frequency range of stored ions.

The second trapping region in segment 517 is designed with entrance apertures on at least two of the pole-electrodes to allow for externally generated ions, electrons, photons and radicals to be injected and react with ions preselected in segment 514, or using the QMF 503. Preferably, the trapping waveform is substantially square to generate a constant trapping field during half of the waveform period to inject ions or electrons with precise kinetic energy. Other trapping waveforms designed with three voltage states can be employed to facilitate external injection of charged species with variable energies. Positive and negative ions or electrons can be injected simultaneously, sequentially or independently through the entrance apertures to activate, ionize, react and dissociate selected ions. The length of segment 517 is reduced compared to 514 to allow for greater axial compression to increase charge density and maximize interaction with externally injected species.

The third trapping region in segment 521 is designed to store and accumulate product ions from consecutive processing steps performed in the LQIT 501. Additional activation can be performed in this segment using photons directed perpendicular through the ion trap axis escaping through window ports attached to the vacuum compartment. Accumulated ions are then released from segment 521 back to the ejection trap 507 for analysis using the orbitrap 510.

The switching sequence of the DC electrical potential profile during an example of a processing cycle 523 is described in FIG. 5 where ions 527 released from the ejection trap 507 or selected in the QMF 503 are transferred through the hexapole ion guide 511 into the LQIT 501 and stored in segment 517. The DC potential across the ion trap 524 is raised at the far end segments during injection into the LQIT to facilitate efficient capturing of ions with elevated axial kinetic energy. The arrival time of the ions in the LQIT is preferably synchronized with a gas pulse to kinetically thermalize ions 528 in segment 517 during the pressure transient. DC potentials are subsequently switched 525 to raise the potential energy of the ions 528 to adjust the kinetic energy of interaction with externally injected ions and electrons. Products and remaining precursor ions are transferred back for detection using the orbitrap analyzer 510 by switching the DC potentials 526 to optimize the axial kinetic energy of the ions and maximize capturing efficiency in the ejection trap 507.

In this example of a processing cycle 523, the potential energy of the ions is switched between three different levels in segment 517. The DC potential applied during injection into the LQIT 501 is configured to match the DC potential applied to the ejection trap 507 to avoid collisional activation in the hexapole 511 by keeping axial ion energy below 10 eV. Controlling the interaction energy in ion-ion or ion-electron activation dissociation experiments requires the DC potential applied to segment 517 to be adjusted relative to the kinetic energy of the incoming ions or electrons. Finally, detection of products species using the orbitrap 510 requires ions to be released from a new DC electrical potential level to ensure efficient trapping in the ejection trap 507.

Figure 6:
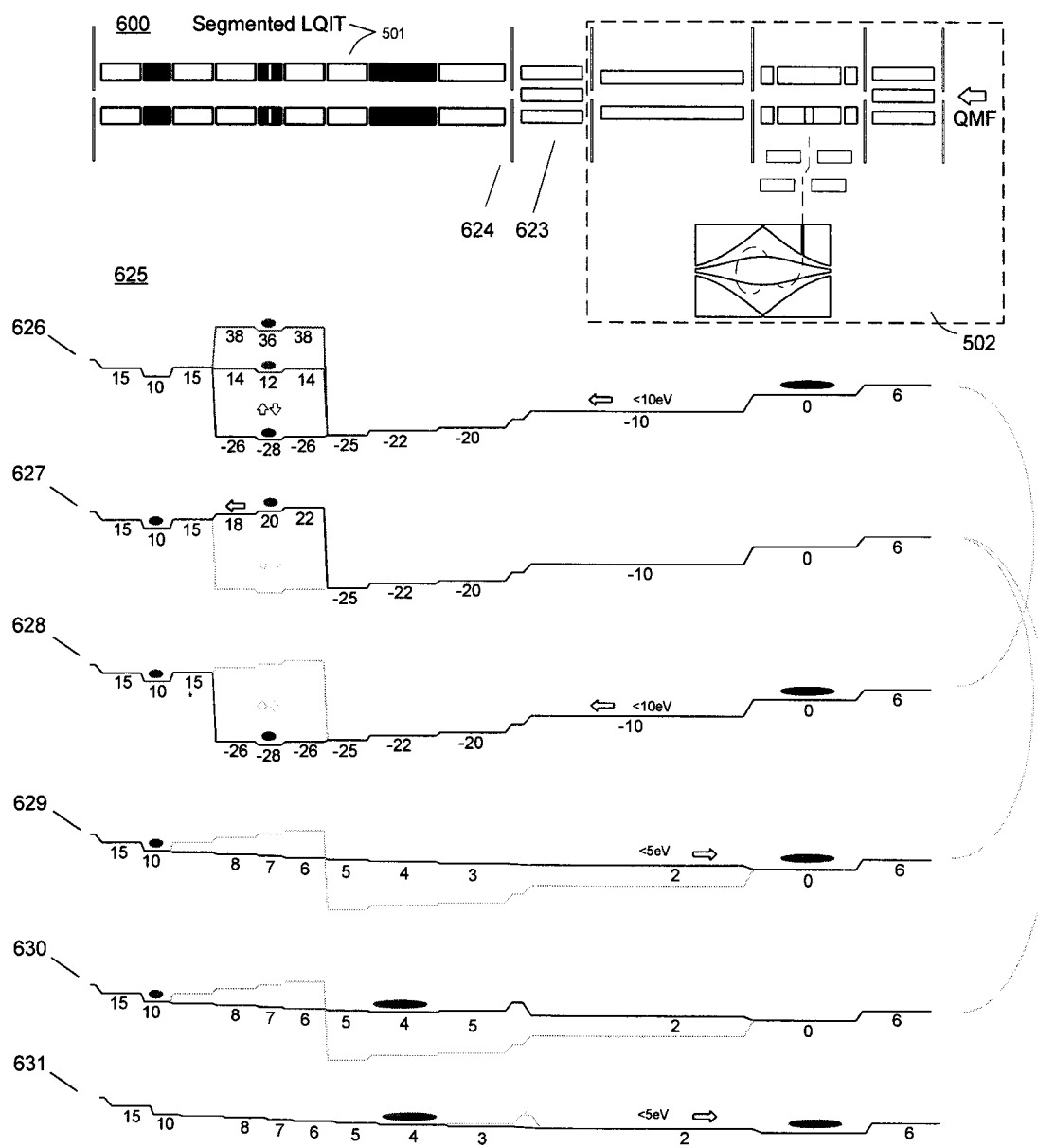
FIG. 6 is a schematic diagram of a mass spectrometer configured with a segmented linear ion trap including the transitions of the DC electrical potential profile to control ion potential energy.

Yet another exemplary embodiment of the present invention is shown in FIG. 6. The schematic diagram of the instrument 600 shows the segmented LQIT 501 attached to a mass spectrometric platform 502 which incorporates an orbitrap mass analyzer 510. An additional bridging hexapole ion guide 623 and a DC lens electrode 624 are disposed between the LQIT and the original ion guide 511 to provide an additional pumping region to reduce the gas load to the orbitrap. The LQIT is differentially pumped and can accommodate heavier gas loads. Light gases such as molecular hydrogen or hydrogen radicals can be admitted to the LQIT at higher densities.

An example of a processing cycle 625 and the corresponding switching sequence of the DC electrical potential profile is also presented in FIG. 6 where ions released from the ejection trap 507 or selected in the QMF 503 are transferred through the ion guide 511 and the bridging hexapole 623 into the LQIT 501 and stored in segment 517. The energy of the interaction between ions and externally injected electrons is controlled by adjusting the DC electrical potential of the trapping region to a single or multiple levels. In this example a third trapping region is formed by adjusting the DC field components in segments 519, 520 and 521 for storing and accumulating ions. Following the activation-dissociation step 626 performed in the second trapping region in segment 517 the potential energy of the ions is raised slightly above the DC potential level of segment 520. Products and remaining precursor ions are transferred with minimum kinetic energy by switching the DC potentials applied to segments 516, 517 and 518, as shown in step 627. The potentials applied to segments 519, 520 and 521 are preferably fixed while the DC potential profile of the remaining segments is adjusted to the original settings 628 to receive a second pulse of ions. Steps 626, 627 and 628 can be repeated until a satisfactory number of product ions have been produced to improve signal-to-noise ratio for low probability or low efficiency dissociation pathways. In this example, following transfer of ions to the third trapping region as shown in step 627 there are two possible options. The first option is to switch the DC potential as shown in step 629 to send product ions back to the ejection trap for mass analysis using the orbitrap. The second option is to transfer ions in the first trapping region for ion isolation and slow heating CID as shown in step 630. Finally, ions are released back to the ejection trap 507 by switching the DC potentials applied to segment 513 and lens electrode 624 as shown in step 631.

Figure 7:
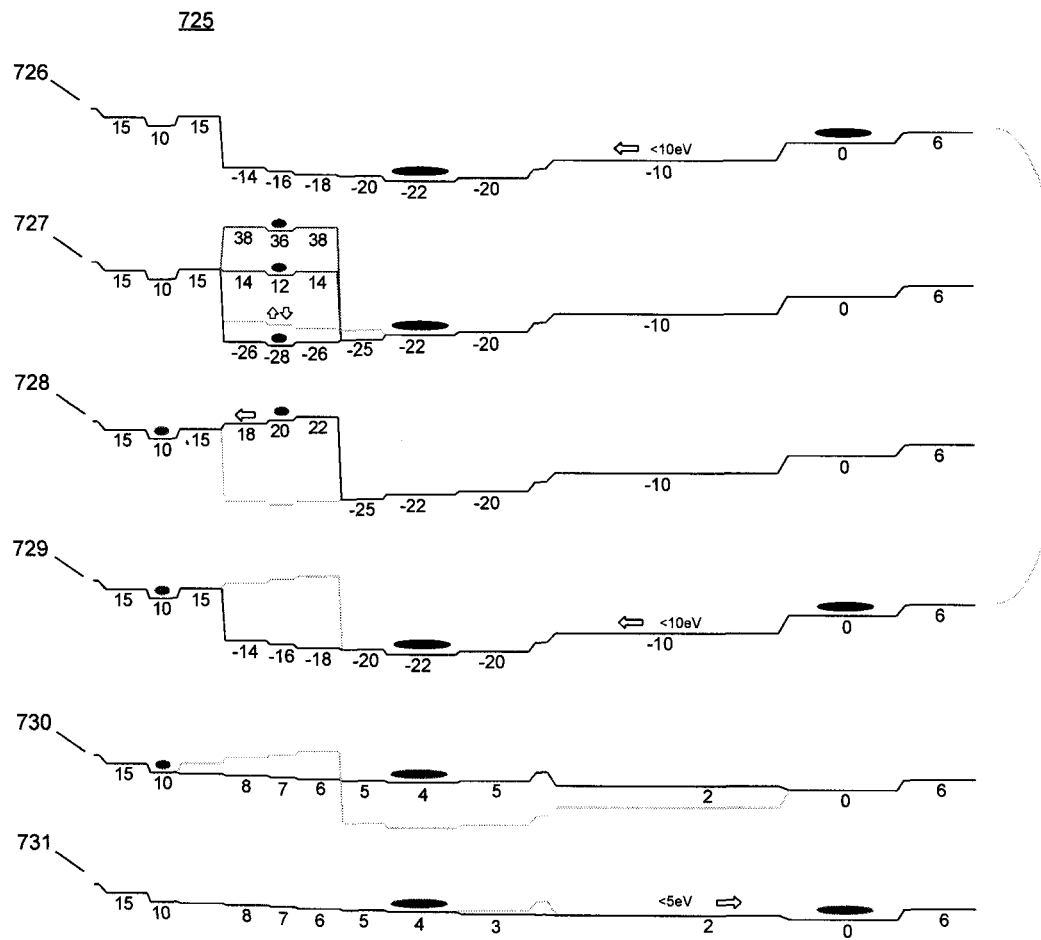
FIG. 7 shows the transitions of the DC electrical potential profile to control ion potential energy for the mass spectrometer shown in FIG. 6.

Another DC potential profile sequence 725 for multiple-stage activation-dissociation experiments performed on the LQIT platform of FIG. 6 is shown in FIG. 7. The DC potentials originally applied to the segments 726 are set to transfer ions to the first trapping region in segment 514 for ion isolation and slow heating CID. It is also desirable to select a single m/z ratio or multiple m/z ratios CID product ions by performing a second isolation step in segment 514. [0092] Segments 515-518 are subsequently switched 727 to transfer selected CID products to the second trapping region in segment 517 where control of the ion potential energy based on the methods disclosed in the present invention is exercised to activate and dissociate ions using externally injected electrons. Second generation products are preferably parked in the third trapping region in segment 520 by adjusting the level of the DC electrical potentials of to potential well and switching the DC field components applied to segments 518, 519 as shown in step 728. The DC profile can be relaxed to the original settings as shown in step 729 to receive a new pulse of ions repeating the processing cycle to accumulate second generation products and improve signal-to-noise ratio during mass analysis. Third generation products can be produced by transferring ions from the third to the first trapping region as shown in step 730. Finally, third generation products are sent back to the ejection trap by switching DC potentials to establish a weak DC gradient to maintain ion kinetic energy below 5 eV.

In processing step 727, the second trapping region is populated with ions and adjusting the DC field components to different levels also alters the potential energy of the ions. Transitions of the DC potential profile can also be performed in regions where ions are not present, as shown for example in processing step 730 where the energy level of the second trapping region is raised to transfer ions between trapping regions under the influence of a weak DC gradient. In another preferred mode of operation efficient transfer is also possible by dropping the potential energy of the ions accumulated in the third trapping region close to the potential level of the second trapping region. Different transitions of the DC field components of the LQIT can be exercised to perform the same processing steps afforded by the highly flexible electronics circuitry of the present invention disclosed in FIG. 3.

Figure 8:
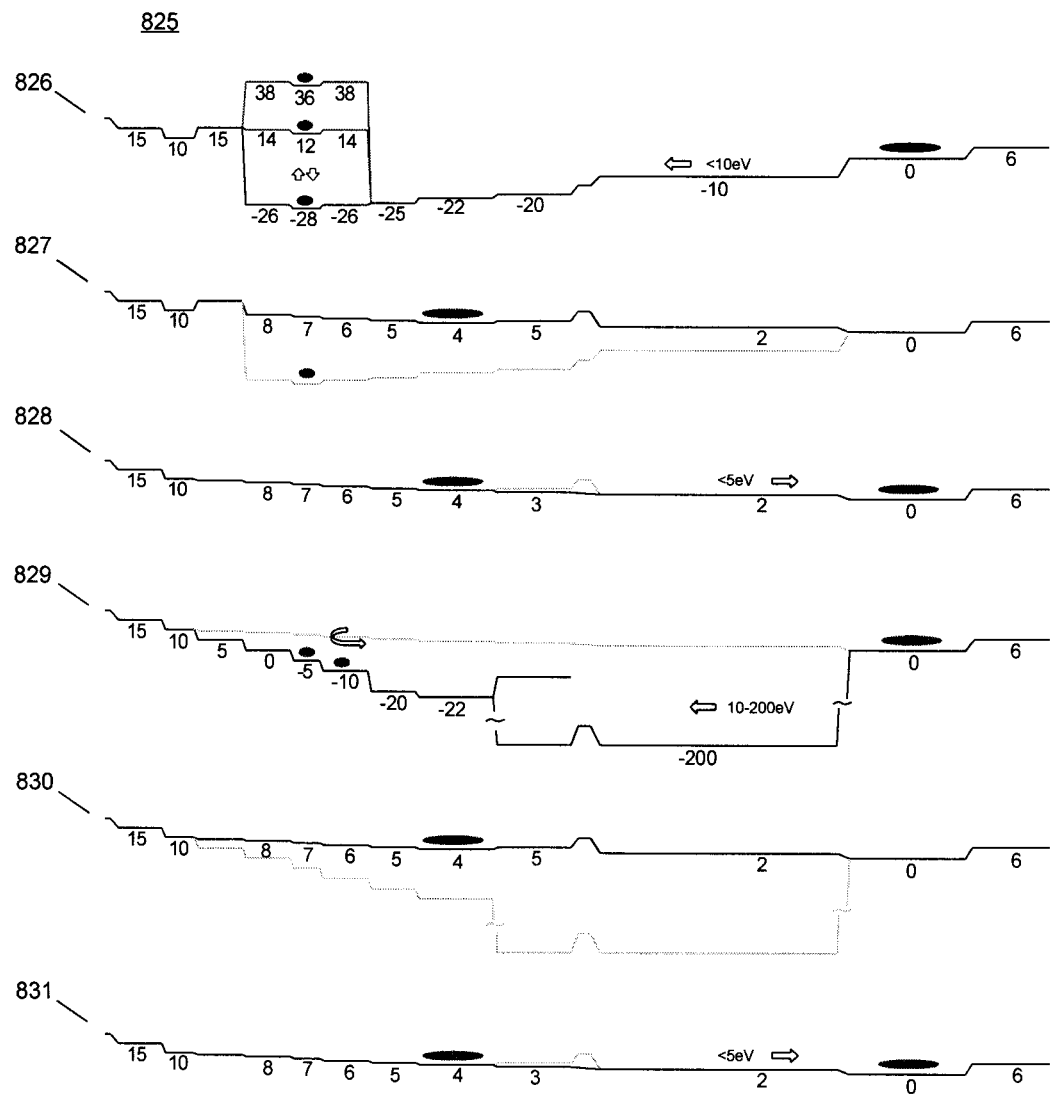
FIG. 8 shows the transitions of the DC electrical potential profile to control ion potential energy for the mass spectrometer shown in FIG. 6.

Yet another processing cycle 825 for multiple-stage activation-dissociation experiments performed on the LQIT platform of FIG. 6 and assisted by potential energy control of the ions is shown in FIG. 8. The DC potentials originally applied to the segments 826 are set to transfer ions to the second trapping region in segment 517 for ion activation using externally injected electrons. Preferably, the potential energy of product ions is dropped prior to switching potentials for transfer. The second processing step 827 involves lifting the potential energy and transferring ions to a neighboring trapping region simultaneously. The lift-transfer method minimizes the energy imparted to ions in collisions with background gas molecules and also minimizes the time required for cooling ions before the next processing step is applied. Faster transitions between processing steps are therefore accomplished reducing the overall time of the processing cycle. In this example of a processing cycle, first generation product ions stored in the first trapping region in segment 514 are processed using isolation waveforms and selected m/z ratios are released back to the ejection trap 828. The DC potentials applied to the RF ion guides 511 and 623 are dropped and ions released axially from the ejection trap undergo energetic collisions with background gas molecules to form second generation high-energy CID products, which are decelerated in the LQIT in the presence of a RF trapping field and a reflecting DC field produced by adjusting the DC field components as shown in step 829. Switching the DC potential applied to segment 513 prevents energetic ions from escaping the LQIT and ions are thermalized in the first trapping region. The potential energy of the ions is raised again 830 and DC potentials are switched 831 to transfer ions to the ejection trap for mass analysis.

The foregoing discussion discloses and describes exemplary methods, electronics circuitries and embodiments of the present invention. As will be understood by those familiar with the art, the invention may be embodied in other specific forms without departing from the spirit or essential characteristics thereof.

For example, the linear ion trap of the present invention can also be configured to accommodate surface induced dissociation experiments by accelerating molecular ions with sufficiently high kinetic energies toward an end-cap electrode positioned at the far end of the linear ion trap and partly immersed in the RF trapping field of a trapping region. Simultaneous switching the DC field components in neighboring segments is preferably applied to store fragment ions therein. Acceleration to high kinetic energies is accomplished by high voltage DC switching applied to the end-cap electrode or to a trap segment. The surface induced dissociation technique can be applied independently or in series with other processing techniques as disclosed in the present invention.

In another example, ions stored in a trapping region of the linear ion trap are ejected into an ion mobility spectrometer for separation based on cross section and charge state. Mobility separated ions can be selected using a gate and transferred back to the linear ion trap for further processing. Transferring ions to the linear ion trap requires lifting the DC electrical potential across the trapping region of the ion mobility spectrometer and switching one or more DC field components forming the trapping region to release ions backwards, similarly to the methodology disclosed in the present invention. The method also requires applying a RF field component for radial confinement of the ions in the trapping region and also reversing the DC gradient across the ion mobility spectrometer.

Accordingly, the disclosure of the present invention is intended to be illustrative, but not limiting, of the scope of the invention, which is set forth in the following claims.

What is claimed is:

1. A linear ion trap comprising:
   at least two discrete trapping regions for processing ions;
   a RF electrical potential generator for producing two RF waveforms, each applied to a pair of pole electrodes of the linear ion trap forming a RF trapping field component to trap ions radially;
   a multi-output DC electrical potential generator producing multiple DC field components superimposed to the RF field component and distributed across the length of the linear ion trap to control ions axially; and
   a control unit configured to switch the DC electrical potentials and corresponding DC field components collectively forming a first trapping region of the at least two discrete trapping regions that is populated with ions to alter an ion potential energy from a first level to a second level, and to enable a first ion processing step in at least one of the first and second levels.

2. The linear ion trap of claim 1, wherein the control unit is further configured to switch at least one DC field component of the multiple DC field components collectively forming the first trapping region between three different DC electrical potential levels.

3. The linear ion trap of claim 2, wherein the control unit is further configured to switch at least one DC field component of the multiple DC field components to transfer ions from the first trapping region to a second trapping region of the at least two discrete trapping regions to enable a second processing step.

4. The linear ion trap of claim 1, wherein the control unit is further configured to switch a plurality of the DC field components, from among the multiple DC field components, which collectively form a second trapping region of the at least two discrete trapping regions to alter the potential energy of ions stored therein from the first level to the second level.

5. The linear ion trap of claim 4, wherein the control unit is further configured to switch at least one DC field component of the multiple DC field components collectively forming the second trapping region between three different DC electrical potential levels.

6. The linear ion trap of claim 1, wherein the RF waveforms comprise substantially rectangular voltage pulse trains.

7. The linear ion trap of claim 1, further comprising a pair of pole electrodes configured to receive a beam of charged particles that are injected through at least one of the two discrete trapping region populated with ions at a first potential energy level.

8. The linear ion trap of claim 1, wherein the control unit is further configured to switch a plurality of the multiple DC field components to release ions from the first trapping region toward a second trapping region with sufficient kinetic energy to perform collision induced dissociation.

9. The linear ion trap of claim 1, wherein the control unit is further configured to switch at least one of the DC field components to eject processed ions toward a mass analyzer for measuring mass-to-charge ratio.

10. A linear ion trap comprising:
at least two discrete trapping regions for activating ions;
at least one gas pulse valve for applying pulses of gas to dynamically control pressure above background in the at least two discrete trapping regions;
a RF electrical potential generator for producing two RF waveforms, each applied to a pair of pole electrodes of the linear ion trap forming a RF trapping field component to trap ions radially;
a multi-output DC electrical potential generator producing multiple DC field components superimposed to the RF field component and distributed across the length of the linear ion trap to control ions axially; and
a control unit configured to switch the DC electrical potentials and corresponding DC field components collectively forming a first trapping region of the at least two discrete trapping regions that is populated with ions to alter ion potential energy from a first level to a second level, and to enable a first ion activation step in at least one of the first and second levels.

11. The linear ion trap of claim 10, wherein the control unit is further configured to enable the first ion activation step during the application of a gas pulse by the at least one gas pulse valve at an elevated gas pressure.

12. The linear ion trap of claim 10, wherein the control unit is further configured to switch at least one DC field component of the multiple DC field components collectively forming the first trapping region between three different DC electrical potential levels.

13. The linear ion trap of claim 10, wherein the control unit is further configured to switch at least one DC field component of the multiple DC field components to transfer ions from the first trapping region to a second trapping region of the at least two discrete trapping regions to enable a second activation step.

14. The linear ion trap of claim 10, wherein the control unit is further configured to switch a plurality of the DC field components, from among the multiple DC field components, which collectively form a second trapping region of the at least two discrete trapping regions to alter the potential energy of ions stored therein from a first level to a second level, and to enable a second ion activation step in at least one of the first and second levels of the second trapping region.

15. The linear ion trap of claim 14, wherein the control unit is further configured to enable the second ion activation step under background pressure.

16. The linear ion trap of claim 15, wherein the control unit is further configured to switch at least one DC field component of the multiple DC field components collectively forming the second trapping region between three different DC electrical potential levels.

17. The linear ion trap of claim 10, wherein the RF waveforms comprise substantially rectangular voltage pulse trains.

18. The linear ion trap of claim 10, further comprising a pair of pole electrodes configured to receive a beam of charged particles that are injected through at least one of the two discrete trapping regions populated with ions at at least a first potential energy level to activate the ions.

19. The linear ion trap of claim 18, wherein the potential energy of the activated ions is switched from the first potential energy level to a second potential energy level to alter the injection energy of the beam of charged particles.

20. The linear ion trap of claim 18, wherein the control unit is further configured to switch at least one of the DC field components to eject the activated ions toward a mass analyzer for measuring mass-to-charge ratio.

21. A linear ion trap comprising:
at least two discrete trapping regions for activating ions;
at least one gas pulse valve for applying pulses of gas to dynamically control pressure above background in the at least two discrete trapping regions;
a RF electrical potential generator for producing two RF waveforms, each applied to a pair of pole electrodes of the linear ion trap forming a RF trapping field component to trap ions radially;
a multi-output DC electrical potential generator producing multiple DC field components superimposed to the RF field component and distributed across the length of the linear ion trap to control ions axially; and
a control unit configured to switch the DC electrical potentials and corresponding DC field components collectively forming a first trapping region of the at least two discrete trapping regions that is populated with ions to alter ion potential energy from a first level to a second level, to enable an activation step under background pressure, to switch at least one DC field component of the multiple DC field components forming the first trapping region to transfer ions from the first trapping region to a second trapping region of the at least two discrete trapping regions, to switch further DC electrical potentials and corresponding DC field components collectively forming the second trapping region to alter ion potential energy from a first level to a second level, and to enable at least one additional activation step in at least one of the first and second levels of the second trapping region during a gas pulse.

* * * * *